(12) United States Patent
Oppenheim et al.

(10) Patent No.: US 6,403,119 B2
(45) Date of Patent: *Jun. 11, 2002

(54) DISCOLORATION-RESISTANT VITAMIN COMPOSITION

(75) Inventors: Richard Charles Oppenheim, Kew; Hung Cam Truong, Chadstone, both of (AU)

(73) Assignee: R. P. Scherer Technologies, Inc., Paradise Valley, NV (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/564,289

(22) Filed: May 4, 2000

(30) Foreign Application Priority Data

Nov. 6, 1997 (AU) ................................ PP0222

(51) Int. Cl.$^7$ ........................... A61K 9/54; A61K 9/52; A61K 9/48
(52) U.S. Cl. .................... 424/458; 424/457; 424/456; 424/451
(58) Field of Search ................ 424/465, 464, 424/451, 452, 458, 456

(56) References Cited

U.S. PATENT DOCUMENTS

| | | | | |
|---|---|---|---|---|
| 4,629,625 A | * | 12/1986 | Gaull | 424/145 |
| 4,695,466 A | * | 9/1987 | Morishita et al. | 424/456 |
| 4,853,229 A | * | 8/1989 | Theeuwes | 424/455 |
| 5,532,002 A | * | 7/1996 | Stroy | 424/456 |
| 5,595,758 A | * | 1/1997 | Adusumilli et al. | 424/456 |
| 6,217,902 B1 | * | 4/2001 | Tanner et al. | 424/456 |

FOREIGN PATENT DOCUMENTS

| | | |
|---|---|---|
| AU | B-27192/84 | 4/1984 |
| GB | 2 298 137 A | 8/1996 |
| JP | 62077320 A | 9/1987 |
| JP | 05139959 A | 9/1993 |
| WO | WO 91/02520 | 3/1991 |
| WO | WO 95/01787 | 1/1995 |

* cited by examiner

Primary Examiner—Thurman K. Page
Assistant Examiner—Rachel M. Bennett
(74) Attorney, Agent, or Firm—Andrew G. Rozycki; Donald O. Nickey

(57) ABSTRACT

The invention disclosed herein includes a vitamin composition encapsulated in a soft or hard shell capsule, said vitamin composition comprising water soluble vitamin particles suspended in a fill liquid, wherein said water soluble vitamin particles are coated with a material that is substantially insoluble in the fill liquid and the shell of the capsule, but soluble in the gastrointestinal tract of a mammal, and the coated water soluble vitamin particles are of a size that are suitable for encapsulating as a suspension in said capsule. The invention also includes a process for manufacturing the same. Vitamin containing capsules according to this invention are discoloration-resistant.

30 Claims, No Drawings

DISCOLORATION-RESISTANT VITAMIN COMPOSITION

FIELD OF THE INVENTION

This application relates to an encapsulated vitamin composition, and is particularly applicable to a vitamin composition encapsulated in a soft gelatin capsule.

BACKGROUND OF THE INVENTION

Soft and hard shell capsules are widely used within the pharmaceutical and health food industry and have gained an acceptance as they present pharmaceutical and health products in a form that is readily consumed and digested by a user. These capsules are generally made up of a shell and an active filling material. The shell is formed of readily digested materials, for example a soft gelatin capsule may comprise a mixture of gelatin, glycerol and water. Hard shell capsules generally comprise gelatin and water. Generally soft and hard shell capsules are suitable for encapsulating a wide range of pharmaceutical and health products in the form of a suspension.

Water soluble vitamins such as the B group vitamins, and Ascorbic Acid are generally presented in the form of a suspension in edible oil when encapsulated in a soft gelatin or hard shell capsule. Oils such as Soya Bean Oil are generally used. The vitamins may be used on their own as the active ingredient, or in combination with herbal materials such as Bioflavanoids, Rutin etc; or with other vitamins. Ascorbic Acid for example, may be combined with other vitamins such as B groups, Betacarotene, Vitamin D and Vitamin E etc; or with minerals such as trace elements of iron, calcium, magnesium and zinc etc. Soft gelatin capsules containing vitamins such as Ascorbic Acid are used for a number of therapeutic and complementary medicine purposes, for example as a component in anti-oxidant therapy in conjunction with Betacarotene and Vitamin E.

Ascorbic Acid has been formulated in a soft gelatin capsule for some time. Generally, when such capsules are presented in the market place they are prepared with opaque shell coloring. Ascorbic Acid and other water-soluble vitamins, such as the B group vitamins, however have a finite solubility in the shell and can migrate from the filling material to the shell if not completely insolubilised. Over time, the water soluble vitamin in the shell may oxidise or may react with the shell causing the shell to darken. The amount needed to cause this darkening can be quite small. The darkening will not effect the overall assay of the capsule, however it can become unsightly. For this reason, generally dark, opaque shells are used to encapsulate Ascorbic Acid and B group vitamin compositions to hide the darkening of the shell. The darkening precludes the use of light colours such as citrus colours for the shell, such as yellow, orange or lime coloring.

SUMMARY OF THE INVENTION

The present invention overcomes, resists or at least alleviates one or more of the difficulties associated with the discoloration of vitamin-containing capsules.

Applicants have found that water soluble vitamin particles, such as Ascorbic Acid particle, that were coated with a material that did not dissolve in both the fill liquid excipients (such as oil based solutions or other encapsulatable liquid based systems) and the shell of the soft or hard shell capsule, but were still able to dissolve from the vitamin particle in the gastrointestinal tract, overcame the disadvantages of discoloration of the shell. Ascorbic Acid particles that are available for use in tablet form can be coated, but have a much larger particle size than what would be suitable for use as a filling material for a soft gelatin or hard shell capsule.

Accordingly, in a first aspect, the present invention resides in a vitamin composition encapsulated in a soft or hard shell capsule, said vitamin composition comprising water soluble vitamin particles suspended in a fill liquid, wherein;

said water soluble vitamin particles are coated with a material that is substantially insoluble in the fill liquid and the shell of the capsule, but soluble in the gastrointestinal tract of a mammal, and the coated water soluble vitamin particles are of a size that are suitable for encapsulating as a suspension in said capsule; wherein said composition and capsule resist discoloration.

The present invention also resides in a process for manufacturing a soft or hard shell capsule containing a coated vitamin composition and which resists discoloration, including the steps of:

(i) providing water soluble vitamin particles which have been coated with a material that is insoluble in a fill liquid and the shell of a soft or hard shell capsule, but soluble in the gastrointestinal tract of a mammal, wherein the coated water soluble vitamin particles are of a size that are suitable for encapsulating as a suspension in the capsule;

(ii) suspending the coated vitamin particles in a compatible fill liquid; and (iii) encapsulating the vitamin composition in a soft or hard shell capsule to produce the vitamin composition as hereinbefore described.

DETAILED DESCRIPTION OF THE INVENTION

Most preferably the capsule is a soft gelatin capsule comprising gelatin, a suitable polyol and water. The suitable polyol is preferably glycerol. Although soft gelatin capsules are preferred, the advantages of the invention are applicable to other soft shell capsules and hard shell capsules, and compositions encapsulated in hard shell capsules also form part of the invention.

Water soluble vitamins that have found to be suitable for use in this invention are the B group vitamins namely Thiamine, Riboflavin, Folic Acid, Biotin, Nicotinic Acid, Pantothenic Acid, Pyridoxine, Cyanocobalamine and Lipoic Acid and Vitamin C, namely Ascorbic Acid. The invention has been found to be particularly applicable for use with Ascorbic Acid.

The fill liquids of the invention may be any liquid based system that is encapsulatable in a soft or hard shell capsule. The coating material may be either hydrophobic or hydrophilic in nature. The selection of the fill liquid for encapsulation will depend upon the nature of the coating material used. For example, if the coating material is hydrophobic, a hydrophilic fill liquid, such as Macrogol 400 will preferably be used. If the coating material is hydrophilic, a hydrophobic fill liquid will preferably be used, such as Soya Bean Oil. This will ensure that the coating material will be insoluble in the fill liquid.

Preferred hydrophobic fill liquids include vegetable oil, vegetable oil derivatives or medium chain triglycerides or mixtures thereof. Suitable vegetable oils include Almond Oil; Arachis Oil; Borage Oil; Canola Oil; Evening Primrose Oil; Fractionated Coconut Oil; Lecithin; Linseed Oil; Maize Oil; Olive Oil; Rapeseed Oil; Rice Bran Oil; Safflower Oil; Soya Bean Oil; Spearmint Oil; Sunflower Oil or Wheatgerm Oil.

Preferred hydrophilic fill liquids include polyethylene glycols having a molecular weight of from 300 to 8,000 or mixtures of polyethylene glycol with other polyols. Most preferred hydrophilic fill liquids include Macrogol 400 and mixtures of Macrogol 400 and propylene glycol and/or glycerol.

The coating material may comprise any material having the requisite properties of insolubility in the fill liquid and the shell of the capsule, whilst being able to disassociate from the particle in the gastrointestinal tract.

The selection of the fill liquid is determined by the solubility of coating material in the fill liquid. Whereas this is largely determined by the hydrophobic/hydrophilic nature of the fill liquid, it has been found that some hydrophobic coating materials remain insoluble in hydrophobic fill liquids. For example, some hydrogenated vegetable oils remain insoluble in a hydrophobic fill liquid such as Soya Bean Oil. Similarly some hydrophilic coating materials will remain insoluble in polyethylene glycol fill liquids.

Whereas it is preferred to select the fill liquid by its hydrophobic/hydrophilic nature, the selection of the fill liquid is determined by the solubility of the coating material in the fill liquid.

Suitable hydrophilic coating materials include glycols and polyglycols having a molecular weight of from 1000–8000. Preferred hydrophilic coating materials include lower alkoxy glycols and lower alkoxy polyglycols, for example, a most preferred material is polyethoxy glycol.

Suitable hydrophobic coating materials include vegetable oil derivatives, fatty acids, fatty acid derivatives including polyoxy ethylene derivatives or fatty oils. Most preferred are hydrogenated vegetable oils, for example derivatives based on Arachis, Coconut or Soya Bean Oils.

The selection of an appropriate fill liquid is essential to ensure that the coating material will remain insoluble within the fill liquid and the shell of the capsule. For this reason it is preferred that if the coating material is essentially hydrophilic in nature, the fill liquid will be hydrophobic. If the coating material is essentially hydrophobic in nature, the fill liquid will preferably be hydrophilic.

In some circumstances, the coating material may contain a mixture of materials, including a mix of hydrophilic and hydrophobic materials. In such circumstances the selection of fill liquid is determined by the overall nature of the coating material and whether that coating material will remain insoluble in the fill liquid. It is however anticipated that the coating material will be essentially either hydrophilic or hydrophobic in nature.

The shell of some soft and hard shell capsules may be considered to be slightly hydrophilic in nature. It has been found that the preferred hydrophilic and hydrophobic coating materials of the invention remain substantially insoluble against the shell of the soft or hard shell capsule. It is only appropriate to use coating materials that are substantially insoluble against the shell of the capsule.

The coating material should be continuous surrounding the vitamin particle to avoid leaching of the vitamin. Preferably, the coating material comprises at least 10% w/w of the coated vitamin particle. More preferably the coating material comprises between 10% w/w and up to 50% w/w of the coated particle and most preferably about 30% w/w.

The coated vitamin particle size may be of any size that is suitable for encapsulation as a suspension in a soft or hard shell capsule. Preferably the particle size is 300 $\mu$m or less however larger particle sizes are also contemplated. Most preferably, the particle size is 180 $\mu$m or less. As the vitamin composition is presented as a suspension, the particle size of the coated vitamin particle should be appropriate for encapsulation as a suspension in a soft or hard shell capsule.

The coated vitamin particle may be produced by first coating the particles and then obtaining the correct particle size upper limit by sieving out the bigger particles. The coating may also be achieved by admixing the coating material and the vitamin, however an inferior result is generally achieved unless a continuous coating of the particle is achieved and aggregates of the particles are removed.

The fill liquid may also include other suspending/dispersing agents such as fatty acids, lecithins and wax mixtures if the fill liquid is hydrophobic, or higher molecular weight dispersing agents such as Macrogol 8000 if a hydrophilic fill liquid excipient is used.

The soft or hard shell capsule may include any suitable amount of vitamin particles in suspension, but generally will include from 10 mg to 1000 mg of vitamin as an active ingredient. The vitamin composition may include a mixture of coated vitamin particles or a combination of coated particles and other coated or uncoated active ingredients.

During the manufacturing process, it is most preferred that the coated vitamin particle is not milled by a high shear process prior to encapsulation in the soft or hard shell capsule. Milling the coated particles by high shear processes may cause the coating material to crack, which can lead to migration of the vitamin material to the shell. Generally a continuous coating is maintained if the coated particle is not milled by high shear processes prior to encapsulation.

The present invention also resides in a process for manufacturing a soft or hard shell capsule containing a coated vitamin composition including the steps of:
(i) providing water soluble vitamin particles which have been coated with a material that is insoluble in a fill liquid and the shell of a soft or hard shell capsule, but soluble in the gastrointestinal tract of a mammal, wherein the coated water soluble vitamin particles are of a size that are suitable for encapsulating as a suspension in the capsule;
(ii) suspending the coated vitamin particles in a compatible fill liquid; and
(iii) encapsulating the vitamin composition in a soft or hard shell capsule to produce the vitamin composition as hereinbefore described.

It is a particular advantage of the present invention that any darkening of the shell by the vitamin is avoided. Therefore this avoids the need to utilise dark shell colours when encapsulating the vitamin. Although conventional shell colours may be used, the shell of the soft or hard shell capsule of the invention may also be coloured to reflect citrus fruits, for example colours such as yellow, orange and lime may be used. Other light colours may also be used. The shell may also be clear or clear coloured. Fruit flavours, odours, perfumes and other additives may also be used as an additive to the shell material. This is particularly advantageous when encapsulating Ascorbic Acid.

The present invention will now be described with reference to the following examples. It should be appreciated that these examples are merely illustrative of the present invention and that the present invention should not be considered to be limited thereto.

EXAMPLE 1

Some pilot filling material consisting of a coated Ascorbic Acid composition, Soya Bean Oil and a suspending/dispersing wax mixture was encapsulated in a soft gelatin capsule. The soft gelatin capsule shell comprised a mixture of gelatin, glycerol and water. The particles were coated with a fat composition of either 10, 20 and 30% w/w. As a control, uncoated Ascorbic Acid was used in a similar suspending solution and encapsulated in a similar soft gelatin capsule. The capsules were placed within a sealed HDPE bottle.

The following Table represents the results of shell discolouration after six weeks stored at different temperatures.

TABLE I

| | Comparative Discolouration | | |
|---|---|---|---|
| | 40° C. | 30° C. | 5° C. |
| Control | Significant | Significant | None |
| 10% w/w | Some | Some, but less than at 40° C. | None |
| 20% w/w | Slight | Slight, but less than at 40° C. | None |
| 30% w/w | None | None | None |

The results show that with a 30% w/w there was no leaching of the Ascorbic Acid to this shell material. Whereas there was some slight discolouration at 20% w/w that discolouration was within acceptable levels. There was some discolouration with the 10% w/w coated particle which may indicate that the particle coating was not continuous.

At 30° C., the results were in the same order but to a less extent than at 40° C. At 5° C. there was no discolouration noticed in any of the capsules.

EXAMPLE 2

The stability trials for the Ascorbic Acid composition described in Example 1 continued over a ten month period. Shell darkening occurred in all lots however there was an appreciable difference between the shell darkening in those compositions where the Ascorbic Acid particle was coated. Those capsules that contained particles of 30% w/w showed the least darkening.

The trial over the ten month period demonstrated that the capsule containing uncoated (0%) particles are appreciably darker than those capsules that contain coated Ascorbic Acid particles. As anticipated those particles that have been subjected to 40° C. heat and 75% relative humidity show appreciably more darkening than those capsules that have not been subjected to such heat, however the capsules that contain coated particles show less darkening even under those adverse temperature conditions. Relatively little darkening occurred in those capsules that had been coated with 10%, 20% and 30% w/w of coating material at 30° C. while even less darkening occurred at 5° C.

Finally, it should be appreciated that many variations, modifications and alterations may be made to the above described composition without departing from the spirit or ambit of the invention.

What is claimed is:

1. A vitamin composition encapsulated in a soft or hard shell capsule, said vitamin composition comprising water soluble vitamin particles suspended in a fill liquid, wherein;
    said water soluble vitamin particles are coated with a material that is substantially insoluble in said fill liquid and the shell of said capsule, but soluble in the gastrointestinal tract of a mammal, whereby the discolouration of the shell by the vitamin particles is reduced; and
    the coated water soluble vitamin particles are of a size that are suitable for encapsulating as a suspension in said capsule; and
    wherein when the coating material is hydrophilic the fill liquid is hydrophobic, and when the coating material is hydrophobic the fill liquid is hydrophilic.

2. A vitamin composition according to claim 1 wherein the capsule is a soft gelatin capsule.

3. A vitamin composition according to claim 1 wherein the water soluble vitamin is selected from thiamine, riboflavin, nicotinic acid, pantothenic acid, pyridoxine, biotin, folic acid, cyanocobalamin, lipoic acid and ascorbic acid.

4. A vitamin composition according to claim 3 wherein the water soluble vitamin is Ascorbic Acid.

5. A vitamin composition according to claim 1 wherein the fill liquid is hydrophobic.

6. A vitamin composition according to claim 5 wherein the fill liquid is a vegetable oil, vegetable oil derivative or a medium chain triglyceride or mixtures thereof.

7. A vitamin composition according to claim 6 wherein the fill liquid is selected from almond oil, arachis oil, borage oil, canola oil, evening primrose oil, fractionated coconut oil, lecithin, linseed oil, maize oil, olive oil, rapeseed oil, rice bran oil, safflower oil, soya bean oil, spearmint oil, sunflower oil or wheatgerm oil.

8. A vitamin composition according to claim 1 wherein the coating material is hydrophilic.

9. A vitamin composition according to claim 8 wherein the coating material is selected from a glycol, a polyglycol or a polyglycol derivative having a molecular weight of from 1000–8000.

10. An encapsulated vitamin composition according to claim 9 wherein the coating material is a lower alkoxy glycol, a lower alkoxy polyglycol, a polyalkoxy or a polyalkoxy derivative.

11. A vitamin composition according to claim 10 wherein the coating material is a polyethoxy glycol.

12. A vitamin composition according to claim 1 wherein the fill liquid is hydrophilic.

13. A vitamin composition according to claim 12 wherein the fill liquid is selected from a polyethylene glycol having a molecular weight of from 300 to 8,000 or a mixture of a polyethylene glycol with other polyols.

14. A vitamin composition according to claim 13 wherein the fill liquid comprises polyethylene glycol having a molecular weight of 400, or a mixture of a polyethylene glycol having a molecular weight of 400 together with propylene glycol, glycerol, or propylene glycol and glycerol.

15. A vitamin composition according to claim 12 wherein the coating material is a vegetable oil derivative, fatty acid, a fatty acid derivative or a fatty oil.

16. A vitamin composition according to claim 15 wherein the coating material is a hydrogenated vegetable oil.

17. A vitamin composition according to claim 1 further including a suspending/dispersing agent.

18. A vitamin composition according to claim 17 wherein the suspending dispersing agent is selected from fatty acids, lecithins and wax mixtures or mixtures thereof if the fill liquid is hydrophobic, and a high molecular weight polyethylene glycols or a high molecular weight polyoxyethylene if the fill liquid is hydrophilic.

19. A vitamin composition according to claim 18 wherein the high molecular weight polyethylene glycol comprises a polyethylene glycol having a molecular weight of 8000.

20. A vitamin composition according to claim 1 wherein the coated water soluble vitamin particle size is less than 300 μm.

21. A vitamin composition according to claim 20 wherein the coated water soluble vitamin particles are a coated Ascorbic Acid particle and have a particle size of less than 180 μm.

22. A vitamin composition according to claim 1 wherein the coating material comprises at least 10% by weight of the coated vitamin particle.

23. A vitamin composition according to claim 22 wherein the coating material comprises from 10% to 50% by weight of the coated vitamin particle.

24. A vitamin composition according to claim 23 wherein the coating material comprises approximately 30% by weight of the coated vitamin particle.

25. A vitamin composition according to claim 2 wherein the shell of the soft gelatin capsule comprises a mixture of gelatin, a suitable polyol and water.

26. A vitamin composition according to claim 25 wherein the polyol is glycerol.

27. A vitamin composition according to claim 1 wherein the shell of the capsule is either opaque or clear colored in a citrus or light color.

28. A vitamin composition according to claim 1 wherein the capsule contains from 10 mg to 1000 mg of active vitamin material.

29. A process for manufacturing a capsule containing a coated vitamin composition and which resists discoloration of the capsule shell caused by the vitamin, including the steps of:

(i) providing water soluble vitamin particles which have been coated with a material that is insoluble in a fill liquid and the shell of a soft or hard shell capsule, but soluble in the gastrointestinal tract of a mammal, wherein the coated water soluble vitamin particles are of a size that are suitable for encapsulating as a suspension;

(ii) suspending the coated vitamin particles in a compatible fill liquid; and encapsulating the vitamin composition in a soft or hard shell capsule;

(iii) wherein when the coating material is hydrophilic, the fill liquid is hydrophobic, and when the coating material is hydrophobic the fill liquid is hydrophilic.

30. A vitamin composition according to claim 1 wherein the vitamin is Ascorbic Acid and the capsule is a soft gelatin capsule.

* * * * *